United States Patent
Artsyukhovich et al.

(10) Patent No.: US 9,314,374 B2
(45) Date of Patent: Apr. 19, 2016

(54) STROBOSCOPIC OPHTHALMIC ILLUMINATOR

(75) Inventors: Alexander N. Artsyukhovich, Irvine, CA (US); Mikhail Boukhny, Laguna Niguel, CA (US); Bruno Dacquay, Irvine, CA (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 452 days.

(21) Appl. No.: 12/727,947

(22) Filed: Mar. 19, 2010

(65) Prior Publication Data

US 2011/0230728 A1    Sep. 22, 2011

(51) Int. Cl.
- A61B 1/06 (2006.01)
- A61F 9/007 (2006.01)
- A61B 1/00 (2006.01)
- A61B 17/00 (2006.01)

(52) U.S. Cl.
CPC ......... A61F 9/00745 (2013.01); A61B 1/00165 (2013.01); A61B 2017/00154 (2013.01); A61B 2017/00194 (2013.01)

(58) Field of Classification Search
USPC .................. 351/221; 600/160–183, 247–249; 606/107, 79–85
See application file for complete search history.

(56) References Cited

U.S. PATENT DOCUMENTS

| | | | |
|---|---|---|---|
| 3,026,449 A * | 3/1962 | Rappaport | 315/166 |
| 4,222,375 A | 9/1980 | Martinez | |
| 4,646,754 A * | 3/1987 | Seale | A61B 3/16 600/402 |
| 4,656,508 A | 4/1987 | Yokota | |
| 4,870,952 A | 10/1989 | Martinez | |
| 4,883,333 A | 11/1989 | Yanez | |
| 4,884,133 A | 11/1989 | Kanno et al. | |
| 5,086,378 A | 2/1992 | Prince | |
| 5,301,090 A | 4/1994 | Hed | |
| 5,420,768 A | 5/1995 | Kennedy | |
| 5,465,170 A | 11/1995 | Arimoto | |
| 5,526,190 A | 6/1996 | Hubble, III et al. | |
| 5,591,160 A | 1/1997 | Reynard | |
| 5,598,042 A | 1/1997 | Mix et al. | |
| 5,634,711 A | 6/1997 | Kennedy et al. | |
| 5,657,116 A | 8/1997 | Kohayakawa | |
| 5,736,410 A | 4/1998 | Zarling et al. | |
| 5,830,139 A | 11/1998 | Abreu | |

(Continued)

FOREIGN PATENT DOCUMENTS

| | | |
|---|---|---|
| EP | 1114608 B1 | 3/2003 |
| JP | 2006087764 A | 4/2006 |

(Continued)

OTHER PUBLICATIONS

Yasujima, H., et al.; JP2006087764A; Publication Date Apr. 6, 2006; Abstract only—machine translation; www.espacenet.com'.

(Continued)

*Primary Examiner* — Jan Christopher Merene
*Assistant Examiner* — Steven Cotroneo
(74) *Attorney, Agent, or Firm* — Jason Finch

(57) ABSTRACT

An ophthalmic illuminator is provided that includes a pulse generator to provide amplified pulses and an amplifier to amplify the current pulses to produce amplified pulses. A light source within the ophthalmic illuminator is driven by the amplified pulses so as to stroboscopically illuminate a vibrating ophthalmic surgical tool within the interior of an eye.

20 Claims, 4 Drawing Sheets

(56) References Cited

U.S. PATENT DOCUMENTS

| | | | |
|---|---|---|---|
| 5,859,693 A | 1/1999 | Dunne et al. |
| 5,997,163 A | 12/1999 | Brown |
| 6,000,813 A | 12/1999 | Krietzman |
| 6,015,403 A | 1/2000 | Jones |
| 6,036,683 A | 3/2000 | Jean et al. |
| 6,102,696 A | 8/2000 | Osterwalder et al. |
| 6,120,460 A | 9/2000 | Abreu |
| 6,123,668 A | 9/2000 | Abreu |
| D434,753 S | 12/2000 | Druckenmiller et al. |
| 6,183,086 B1 | 2/2001 | Neubert |
| 6,190,022 B1 | 2/2001 | Tocci et al. |
| 6,211,626 B1 | 4/2001 | Lys et al. |
| 6,213,943 B1 | 4/2001 | Abreu |
| 6,217,188 B1 | 4/2001 | Wainwright et al. |
| 6,226,126 B1 | 5/2001 | Conemac |
| 6,268,613 B1 | 7/2001 | Cantu et al. |
| 6,270,244 B1 | 8/2001 | Naum |
| 6,272,269 B1 | 8/2001 | Naum |
| 6,336,904 B1 | 1/2002 | Nikolchev |
| 6,431,731 B1 | 8/2002 | Krietzman |
| 6,436,035 B1 | 8/2002 | Toth et al. |
| 6,459,844 B1 | 10/2002 | Pan |
| 6,730,940 B1 | 5/2004 | Steranka et al. |
| 6,786,628 B2 | 9/2004 | Steen et al. |
| 6,893,258 B1 | 5/2005 | Kert |
| 6,917,057 B2 | 7/2005 | Stokes et al. |
| 6,960,872 B2 | 11/2005 | Beeson et al. |
| 7,025,464 B2 | 4/2006 | Beeson et al. |
| 7,063,436 B2 | 6/2006 | Steen et al. |
| 7,229,202 B2 | 6/2007 | Sander |
| 7,276,737 B2 | 10/2007 | Camras et al. |
| 7,301,271 B2 | 11/2007 | Erchak et al. |
| 7,325,957 B2 | 2/2008 | Morejon et al. |
| 7,344,279 B2 | 3/2008 | Mueller et al. |
| 7,349,163 B2 | 3/2008 | Angelini et al. |
| 7,403,680 B2 | 7/2008 | Simbal |
| 7,482,636 B2 | 1/2009 | Murayama et al. |
| 7,494,228 B2 | 2/2009 | Harbers et al. |
| 7,556,412 B2 | 7/2009 | Guillermo |
| 7,561,329 B2 | 7/2009 | Zahniser et al. |
| 7,682,027 B2 | 3/2010 | Buczek et al. |
| 7,918,583 B2 | 4/2011 | Chakmakjian et al. |
| 7,990,587 B2 * | 8/2011 | Watanabe | 358/509 |
| 2002/0003928 A1 | 1/2002 | Bischel et al. |
| 2002/0047992 A1* | 4/2002 | Graves et al. | 351/212 |
| 2002/0087149 A1 | 7/2002 | McCary |
| 2002/0137984 A1 | 9/2002 | Chhibber et al. |
| 2003/0112421 A1 | 6/2003 | Smith |
| 2003/0132701 A1 | 7/2003 | Sato et al. |
| 2003/0147254 A1 | 8/2003 | Yoneda et al. |
| 2003/0169603 A1 | 9/2003 | Luloh et al. |
| 2003/0223249 A1 | 12/2003 | Lee et al. |
| 2004/0004846 A1 | 1/2004 | Steen et al. |
| 2004/0090796 A1 | 5/2004 | Steen et al. |
| 2004/0233655 A1 | 11/2004 | Zimmerman et al. |
| 2005/0018309 A1 | 1/2005 | McGuire, Jr. et al. |
| 2005/0024587 A1 | 2/2005 | Somani |
| 2005/0047172 A1 | 3/2005 | Sander |
| 2005/0063171 A1 | 3/2005 | Leitel et al. |
| 2005/0099824 A1 | 5/2005 | Dowling et al. |
| 2005/0110808 A1 | 5/2005 | Goldschmidt et al. |
| 2005/0140270 A1 | 6/2005 | Henson et al. |
| 2005/0190562 A1 | 9/2005 | Keuper et al. |
| 2005/0243539 A1 | 11/2005 | Evans et al. |
| 2005/0270775 A1 | 12/2005 | Harbers et al. |
| 2006/0203468 A1 | 9/2006 | Beeson et al. |
| 2006/0262272 A1 | 11/2006 | Anderson et al. |
| 2007/0102033 A1 | 5/2007 | Petrocy |
| 2007/0133211 A1 | 6/2007 | Yoneda et al. |
| 2007/0213618 A1* | 9/2007 | Li et al. | 600/476 |
| 2007/0219417 A1* | 9/2007 | Roberts et al. | 600/249 |
| 2007/0273290 A1 | 11/2007 | Ashdown et al. |
| 2007/0284597 A1 | 12/2007 | Nawashiro et al. |
| 2007/0291491 A1 | 12/2007 | Li et al. |
| 2008/0030984 A1 | 2/2008 | Harbers et al. |
| 2008/0112153 A1 | 5/2008 | Iwasaki et al. |
| 2008/0144169 A1 | 6/2008 | Zahniser et al. |
| 2008/0175002 A1 | 7/2008 | Papac et al. |
| 2008/0208006 A1 | 8/2008 | Farr |
| 2008/0246919 A1 | 10/2008 | Smith |
| 2008/0246920 A1 | 10/2008 | Buczek et al. |
| 2008/0262316 A1 | 10/2008 | Ajima et al. |
| 2008/0291682 A1 | 11/2008 | Falicoff et al. |
| 2009/0036955 A1 | 2/2009 | Han |
| 2009/0054957 A1 | 2/2009 | Shanbaky |
| 2009/0093750 A1 | 4/2009 | Herman |
| 2009/0095960 A1 | 4/2009 | Murayama |
| 2009/0105698 A1 | 4/2009 | Hodel et al. |
| 2009/0131823 A1* | 5/2009 | Andreyko et al. | 600/567 |
| 2009/0154137 A1 | 6/2009 | Bierhuizen et al. |
| 2009/0154192 A1 | 6/2009 | Krattiger |
| 2009/0168395 A1 | 7/2009 | Mrakovich et al. |
| 2009/0182313 A1 | 7/2009 | Auld |
| 2009/0190371 A1 | 7/2009 | Root et al. |
| 2009/0203966 A1 | 8/2009 | Mizuyoshi |
| 2009/0219586 A1 | 9/2009 | Fujimoto et al. |
| 2009/0227847 A1* | 9/2009 | Tepper et al. | 600/249 |
| 2009/0267088 A1 | 10/2009 | Peng et al. |
| 2010/0100006 A1* | 4/2010 | Xu et al. | 600/562 |
| 2010/0127299 A1 | 5/2010 | Smith et al. |
| 2010/0182569 A1 | 7/2010 | Artsyukhovich et al. |
| 2010/0228089 A1* | 9/2010 | Hoffman | A61B 1/063 600/182 |
| 2010/0317923 A1* | 12/2010 | Endo et al. | 600/178 |
| 2011/0009752 A1* | 1/2011 | Chen et al. | 600/478 |
| 2011/0037949 A1 | 2/2011 | Papac et al. |
| 2011/0038174 A1 | 2/2011 | Papac et al. |
| 2011/0122366 A1 | 5/2011 | Smith |

FOREIGN PATENT DOCUMENTS

| | | |
|---|---|---|
| WO | 00/54655 A1 | 9/2000 |
| WO | 2008/133736 A2 | 11/2008 |

OTHER PUBLICATIONS

Liu, C.K., et al.; "High Efficiency Silicon-Based High Power LED Package Integrated with Micro-Thermoelectric Device"; Microsystems Packaging, Assembly and Circuits Technology, Impact 2007. Abstract only—worldwide web: www.ieee.org; DOI 10.1109/IMPACT.2007.4433562.

* cited by examiner

STROBOSCOPIC OPHTHALMIC ILLUMINATOR

TECHNICAL FIELD

This application relates to illumination in ophthalmic procedures and more particularly to stroboscopic ophthalmic illumination.

BACKGROUND

Ophthalmic illuminators allow a surgeon to illuminate the interior structure of the eye such as the vitreous and the retina during surgical procedures. For example, an endoscopic ophthalmic illuminator (endo-illuminator) includes an optical fiber within the bore of a cannula. By driving a proximal end of the optical fiber with a suitable light source, light emitted from a distal end of the fiber illuminates the desired portion of the eye during a surgical procedure. Alternatively, a physician may illuminate the eye with fiber optic illumination while using an ophthalmic microscope. With the desired portion of the eye sufficiently illuminated, the physician may then perform surgical procedures that may require the use of a vibrating cutting tool such as a ultrasonic handpiece to phaco-emulsify a cataract-clouded lens or an oscillating cutter for vitrectomy procedures.

Despite the presence of ophthalmic illumination, the rapid oscillation for the mechanical cutting tools during such procedures renders significant portions of the operating field blurred with respect to human vision. Not only is the tool itself blurred but the surrounding ocular tissues will also be obscured. Accordingly, there is a need in the art for an improved ophthalmic illuminator for use with vibrating surgical tools.

SUMMARY

In accordance with a first aspect of the disclosure, a stroboscopic ophthalmic illuminator is provided that includes: a pulse generator for generating electrical pulses, an amplifier for amplifying the generated pulses, and a light source driven by the resulting amplified pulses.

In accordance with a second aspect of the disclosure, a stroboscopic endo-illuminator is provided that includes: a pulse generator for generating electrical pulses, an amplifier for amplifying the generated pulses, a light source driven by the resulting amplified pulses, and an optical fiber for receiving light pulses from the light source so as to stroboscopically illuminate an ophthalmic field of operation.

In accordance with a third aspect of the disclosure, a method of stroboscopically illuminating an ophthalmic operating field within a human eye is provided that comprises: vibrating an ophthalmic surgical tool at a tool vibration frequency; generating electrical pulses responsive to the tool vibration frequency; driving a light source responsive to the electrical pulses to produce corresponding light pulses; and transmitting the light pulses into the ophthalmic operating field so as to stroboscopically illuminate the vibrating ophthalmic surgical tool.

DETAILED DESCRIPTION

To allow a surgeon to visualize the cutting motion for vibrating ophthalmic surgical tools, a stroboscopic ophthalmic illuminator is provided. The resulting stroboscopic adaptation may be applied to a wide variety of illuminators such as surgical microscopes, slit lamps, indirect ophthalmoscopes, and fiber endo-illuminators. Thus, although the following discussion will be directed to example embodiments, it will be appreciated that the concepts disclosed herein may be widely applied to other types of ophthalmic illuminators.

Figure 1:
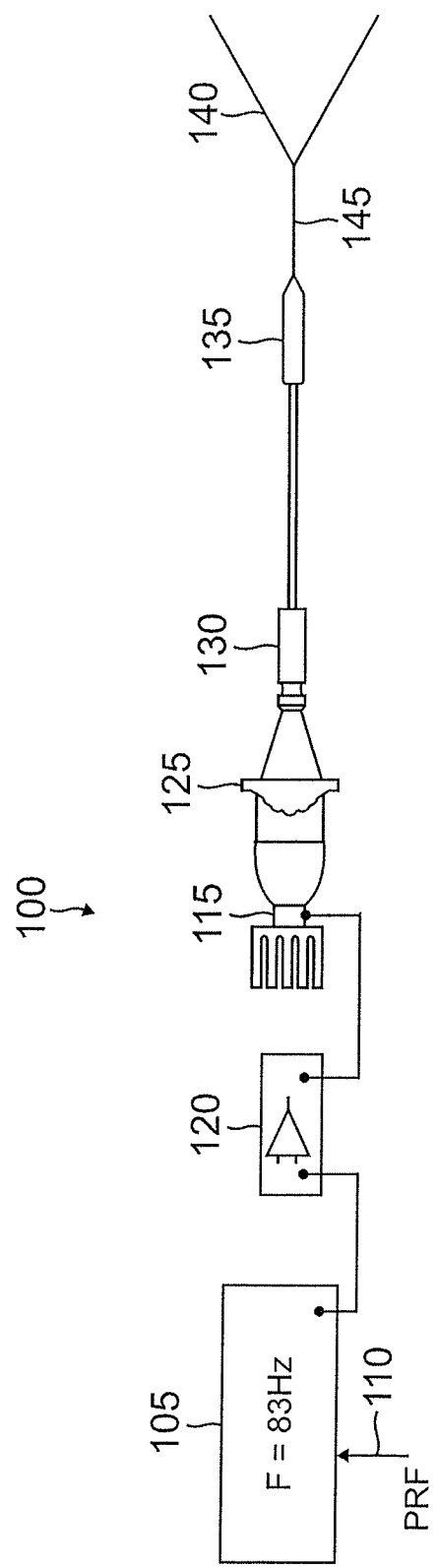
FIG. 1 illustrates a stroboscopic endo-illuminator.

Turning now to the drawings, FIG. 1 illustrates a stroboscopic fiber endo-illuminator 100. Rather than use a conventional DC power source, endo-illuminator 100 is driven by a pulse generator 105. To provide a stroboscopic illumination for a vibrating surgical tool, the pulse repetition frequency (PRF) for the electrical pulses provided by pulse generator 105 is selected responsive to the vibration frequency for the particular vibrating surgical tool being illuminated. Should the surgeon want the tool to appear stationary, the PRF for generator 105 may match the tool's vibration frequency. Alternatively, should the surgeon desire the tool to appear to be moving slowly, the PRF may be slightly slower or faster than the tool's vibration frequency. Pulse generator 105 may thus be responsive to a PRF command 110 such that a surgeon may vary the PRF as desired during the surgical procedure. Pulse generator 105 responds to PRF command 110 to either increase or decrease the PRF as commanded by the physician so as to produce the desired stroboscopic illumination. Alternatively, pulse generator 105 may have a non-user-variable PRF.

The resulting electrical pulses from generator 105 will ultimately drive a light source in fiber endo-illuminator 100 such as a high-power light emitting diode (LED) 115. Conventional high-power LEDs are readily capable of providing light pulses as short as 1 µs. Such a short pulse would correspond to a PRF as high as 1 mega-hertz (MHz), which is well above the conventrionally-required range for phaco-emulsification such as 45 kilo-hertz (kHz). Alternatively, LED 115 may be replaced with other suitable light sources such as a gas discharge source. To provide a sufficient level of luminous flux in the ophthalmic operating field with the relatively short current pulses necessary to make a 5000 cuts per minute (5000 cpm) vibrating victrectomy cutting tool appear to be stationary, an amplifier 120 amplifies the pulses from generator 105 so as to drive LED 115 with amplified electrical pulses at a corresponding PRF of 83 Hz. However, it will be appreciated that amplifier 120 would be unnecessary should the pulse generator provide pulses of sufficient power at such a relatively long pulse length.

An example embodiment for amplifier 120 will be discussed further herein with regard to FIG. 4. Referring again to FIG. 1, endo-illuminator 100 includes optics 125 to focus the resulting light from LED onto the proximal end of an optical fiber(s) within a proximal connector 130. Endo-illuminator 100 also includes a handpiece 135 so that a surgeon may manually direct the pulsed light 140 emitted from a cannula 145. Consider the advantages of pulsed endo-illuminator 100—a surgeon is now able to visualize the movements of the vibrating ophthalmic surgical tool as well as the tissue being dissected by the ophthalmic surgical tool. In this fashion, a surgeon will have additional insight in the operation of the ophthalmic surgical tool and the desired surgical effect caused by its vibration.

Figure 2:
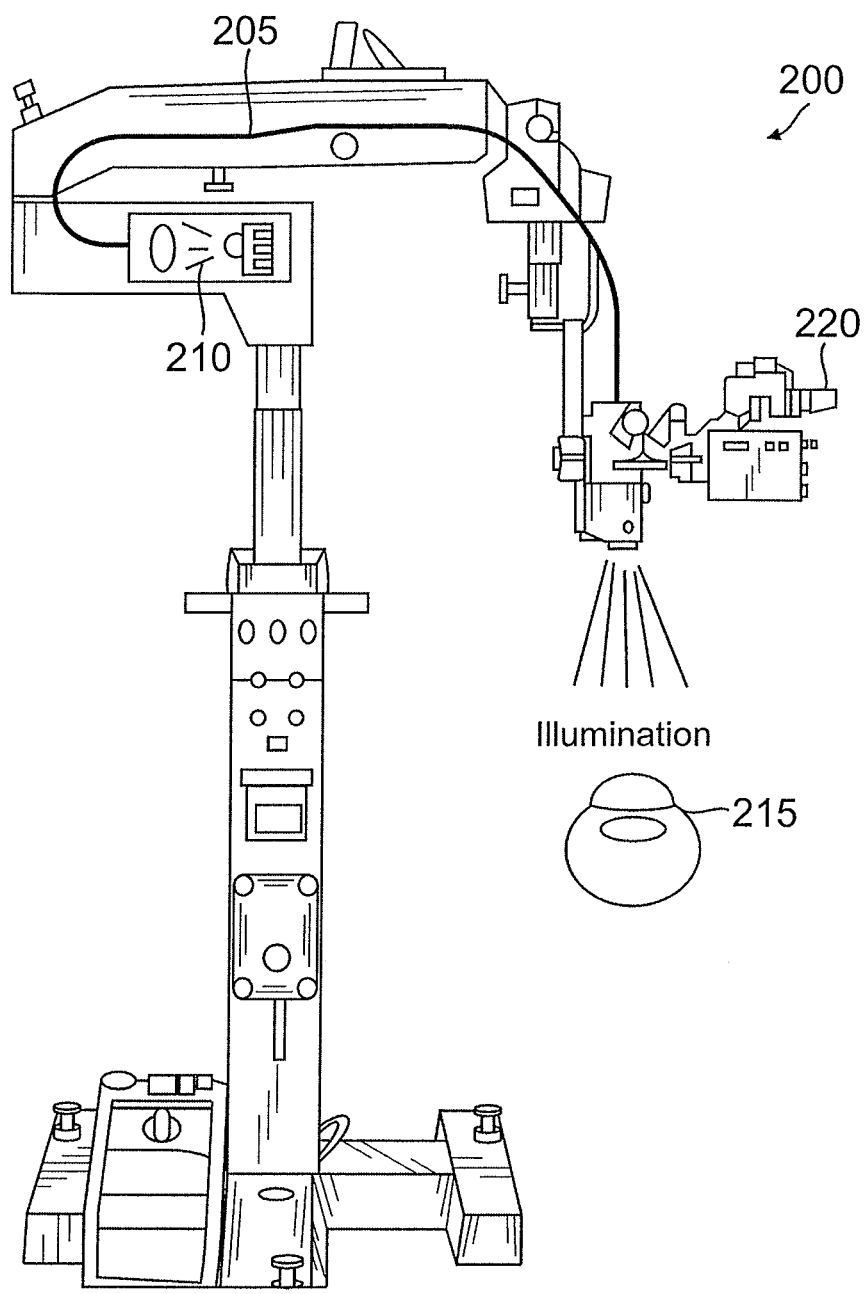
FIG. 2 illustrates a stroboscopically-illuminated ophthalmic microscope.

Although the preceding discussion concerned the stroboscopic modification of a fiber endo-illuminator, the pulse generator and current amplifier of FIG. 1 may be used to drive the light source in a wide variety of other ophthalmic illuminators such as surgical microscopes, slit lamps, and indirect ophthalmoscopes. For example, a stroboscopic ophthalmic microscope 200 is illustrated in FIG. 2. Microscope 200 includes an optical fiber bundle 205 driven by a light source engine 210. Engine 210 includes optics to focus the resulting pulsed light onto fiber bundle 205. Fiber bundle 205 is positioned so that a vibrating ophthalmic surgical tool such as a phaco-emulsification tool within an eye 215 is stroboscopically illuminated as viewed by a physician through eyepieces 220. Engine 210 includes a pulse generator and an amplifier (not illustrated) as analogously discussed with regard to FIG. 1. To allow a physician to alternate between DC and stroboscopic embodiments, the pulse width from the pulse generator may be adjusted such that the pulse generator output is effectively a DC signal.

Figure 3A:
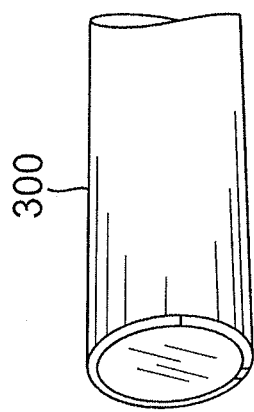
FIG. 3a illustrates a top and side view of a phaco-emulsification tool tip as captured by a stroboscopic flash from the illuminator of FIG. 2 as the tool is displaced towards the top of a vibration cycle.
Figure 3B:
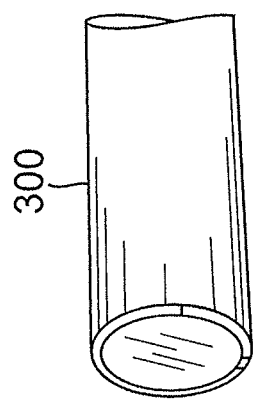
FIG. 3b illustrates a top and side view of a phaco-emulsification tool tip as captured by a stroboscopic flash from the illuminator of FIG. 2 as the tool is displaced towards the middle of a vibration cycle.
Figure 3C:
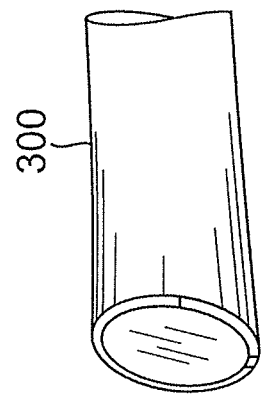
FIG. 3c illustrates a top and side view of a phaco-emulsification tool tip as captured by a stroboscopic flash from the illuminator of FIG. 2 as the tool is displaced towards the bottom of a vibration cycle.

In general, the PRF for a stroboscopic ophthalmic illuminator will depend upon the tool vibration frequency. For example, the vibration frequency for a phaco-emulsification tool illuminated by light source engine 210 of FIG. 2 will range from 30 to 42 kHz or even as high as 50 to 60 kMHz or higher. Stroboscopically-illuminated images of a phaco-emulsification tool tip 200 are shown in FIGS. 3a, 3b, and 3c. To generate these images, an LED is driven by a pulse generator and amplifier as discussed with regard to FIG. 2. Each of FIGS. 3a, 3b, and 3c show both a side view (top images) as well as a longitudinal view into the tool tip lumen (bottom images). In general, tool tip 300 will oscillate through a range of motion such that as seen from the side, the tool tip will vary from a top extreme of motion down through a bottom extreme of motion. As can be seen in FIG. 3a, a surgeon would be able to visualize the tool tip at the top extreme of this range of motion whereas in FIG. 3b, the surgeon is seeing the mid-range position of the tool tip. Finally, as shown by FIG. 3c, the surgeon may see the bottom extreme range of motion for the tool tip. The longitudinal views show how the tool tip twists as it travels through these oscillation ranges. In these figures, the pulse generator is driven at a PRF of 31.375 kHz whereas the phaco-emulsification tool tip was vibrating in the range of 30 to 42 kHz. The mismatch between the pulse generator PRF and the tool vibration frequency results in an apparent vibration frequency of just a few Hz for the tool, thereby enabling a surgeon to see the tool motion. Because neither the PRF from the pulse generator nor the tool vibration frequency will be perfectly constant, it is typical that this apparent vibration frequency will slightly drift over time. To prevent such drift, a surgeon may adjust the PRF frequency as necessary as discussed above. Alternatively, the pulse generator could automatically adjust its PRF responsive to triggering light pulses transmitted from the ophthalmic illuminator. To produce the images shown in FIGS. 3a through 3c, a Lumileds Luxeon K2 with TFFC source was selected as LED 115. However, it will be appreciated that a wide variety of high-power LEDs would also be suitable.

Figure 4:
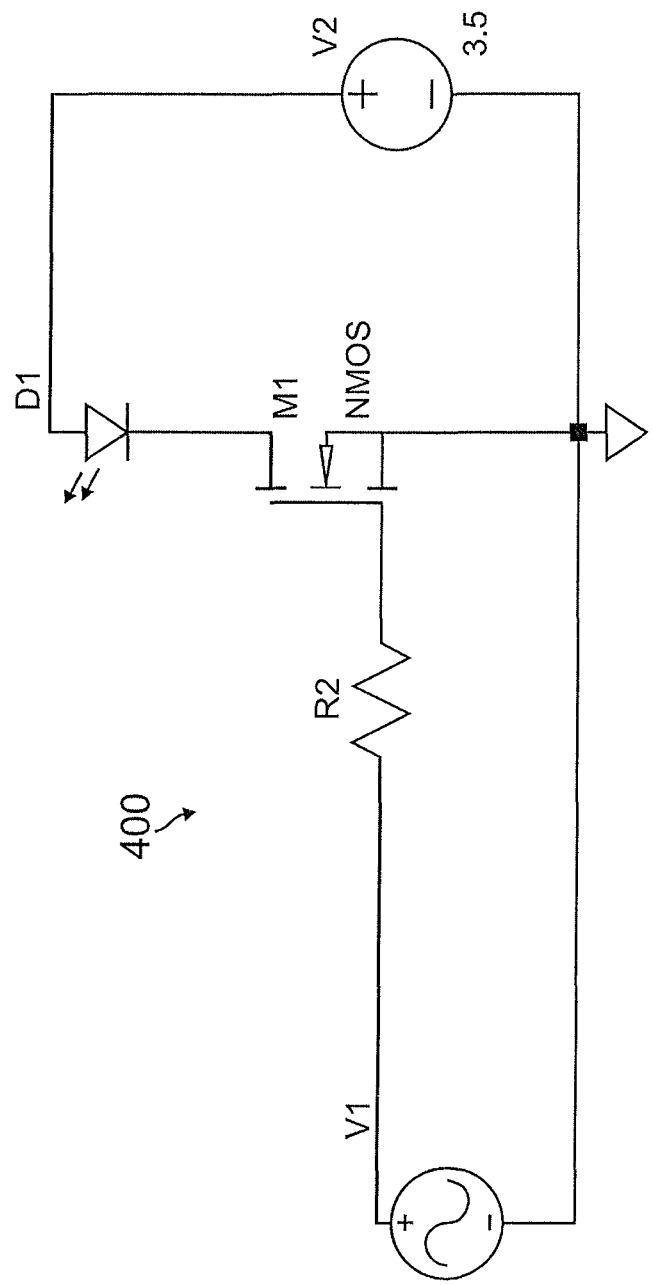
FIG. 4 is a schematic diagram for an amplifier for the ophthalmic illuminators of FIGS. 1 and 2.

Turning now to FIG. 4, an example amplifier 400 is illustrated that is adapted for the relatively high PRF used to capture the images discussed with regard to FIGS. 3a, 3b, and 3c. The pulse generator is represented as a voltage source V1 that generates voltage pulses with respect to electrical ground. The voltage pulses from source V1 drive a power switch such as an NMOS transistor M1. Although amplifier 400 is thus described with respect to an NMOS transistor power switch embodiment, it will be appreciated that amplifier 400 is readily modified to perform with a PMOS transistor switch. Source V1 drives a gate of M1 through a resistor R2 having a suitable resistance such as 200 ohms. The LED source D1 has its cathode coupled to the drain of M1 whereas an anode of the LED source couples to a DC power supply V2. In general, the voltage level for source V2 will depend upon the current rating of the LED source and the PRF for the pulse generator V1. In that regard, as the PRF is increased (shorter pulse periods), the output voltage from DC power supply V2 may be increased so that a sufficient amount of current is driven through the LED during the power switch on times. For example, at a PRF of 1 MHz, the output voltage for power supply V2 may be as high as 20 volts (V). Because the PRF for amplifier 400 is just 31.375 KHz, the output voltage for DC power supply V2 is 3.5 V for such an embodiment. In general, the PRF will depend upon the tool vibration frequency. For example, some phaco-emulsification procedures occur at the 50 to 60 kHz range such that the PRF would have to be increased accordingly. Regardless of the resulting PRF, DC power supply V2 will thus drive a current through LED D1 when the gate of M1 is pulsed by pulse generator V1. In this fashion, LED D1 will be driven with an amplified amount of current as compared to simply driving the LED directly from the pulse generator.

Embodiments described above illustrate but do not limit the invention. It should also be understood that numerous modifications and variations are possible in accordance with the principles of the present invention. Accordingly, the scope of the invention is defined only by the following claims.

What is claimed is:
1. A system comprising:
  a surgical tool comprising a cutting element configured to vibrate at a tool vibration frequency; and
  a fiber endo-illuminator, comprising:
    a pulse generator configured to:
      receive a signal indicating the tool vibration frequency;
      determine, based at least in part on the received signal, a pulse repetition frequency corresponding to the tool vibration frequency to make the cutting element of the surgical tool appear either to be stationary or to be moving at a frequency lower than the tool vibration frequency; and
      provide electrical pulses at the determined pulse repetition frequency;
    an amplifier configured to amplify the electrical pulses to produce amplified pulses;
    a light source driven by the amplified pulses to produce light pulses;
    at least one optical fiber configured to receive the light pulses and to stroboscopically illuminate the cutting element of the surgical tool; and
    the pulse generator is further configured to adjust the pulse repetition frequency in response to triggering light pulses transmitted from the fiber endo-illuminator.

2. The system of claim 1, wherein the light source is an LED.

3. The system of claim 1, wherein the light source is a high-discharge lamp.

4. The system of claim 1, wherein the pulse repetition frequency is determined based at least in part on a received a pulse repetition frequency command.

5. The system of claim 1, further comprising:
a proximal connector for receiving the at least one optical fiber; and
optics for focusing the light pulses onto a proximal end of the at least one optical fiber within the proximal connector.

6. The system of claim 5, further comprising:
a handpiece for manually directing a distal end of the at least one optical fiber.

7. The system of claim 6, wherein the distal end of the at least one optical fiber is contained within a cannula.

8. The system of claim 1, the tool vibration frequency ranging from a low of 30 to 42 kHz to a high of 50 to 60 kHz.

9. A method of stroboscopically illuminating an ophthalmic operating field within a human eye, comprising:
receiving a signal indicating a vibration frequency of a cutting element of an ophthalmic surgical tool;
determining, based at least in part on the received signal, a pulse repetition frequency corresponding to the tool vibration frequency to make the cutting element of the surgical tool appear either to be stationary or to be moving at a frequency lower than the tool vibration frequency;
providing electrical pulses at the determined pulse repetition frequency to a light source operable to generate corresponding light pulses, the corresponding light pulses, when transmitted into the ophthalmic operating field, stroboscopically illuminating the cutting element of the ophthalmic surgical tool; and
adjusting the pulse repetition frequency in response to triggering light pulses received from the ophthalmic operating field.

10. The method of claim 9, wherein the ophthalmic surgical tool is a phaco-emulsification tool.

11. The method of claim 10, wherein the vibration frequency of the cutting element of the ophthalmic surgical tool is in the range of 30 to 80 kHz.

12. The method of claim 9, wherein the determined pulse repetition frequency matches the tool vibration frequency of the cutting element of the ophthalmic surgical tool.

13. The method of claim 9, wherein the ophthalmic surgical tool is a vitrectomy cutting tool.

14. A system comprising:
a surgical tool comprising a cutting element configured to vibrate at a tool vibration frequency; and
an ophthalmic illuminator, comprising:
a pulse generator configured to:
receive a signal indicating the tool vibration frequency;
determine, based at least in part on the received signal, a pulse repetition frequency corresponding to the tool vibration frequency to make the cutting element of the surgical tool appear either to be stationary or to be moving at a frequency lower than the tool vibration frequency; and
provide electrical pulses at the determined pulse repetition frequency;
an amplifier configured to amplify the electrical pulses to produce amplified pulses;
a light source driven by the amplified pulses to stroboscopically illuminate the cutting element of the surgical tool; and
the pulse generator is further configured to adjust the pulse repetition frequency in response to triggering light pulses transmitted from the ophthalmic illuminator.

15. The system of claim 14, wherein the light source is contained within an endo-illuminator.

16. The system of claim 14, wherein the light source is contained within an ophthalmic microscope.

17. The system of claim 16, wherein the light source drives a fiber bundle within the ophthalmic microscope.

18. The system of claim 14, wherein the amplifier includes a switch in series with a power source and an LED light source, the switch being responsive to the electrical pulses so as to turn on and allow the power source to drive current through the LED light source.

19. The system of claim 18, wherein the switch is a transistor switch.

20. The system of claim 14, the tool vibration frequency ranging from a low of 30 to 42 kHz to a high of 50 to 60 kHz.

* * * * *